United States Patent [19]

Michaud

[11] 4,246,901
[45] Jan. 27, 1981

[54] URINE COLLECTION DEVICE

[76] Inventor: Robert A. Frosch, Administrator of the National Aeronautics and Space Administration, with respect to an invention of Roger B. Michaud, League City, Tex.

[21] Appl. No.: 910,992

[22] Filed: May 30, 1978

[51] Int. Cl.³ .................................................. A61F 5/44
[52] U.S. Cl. ..................................... 128/295; 4/144.3; 128/761
[58] Field of Search ............... 128/294, 295, 760, 761, 128/762, 768, 769; 4/144.1, 144.2, 144.3, 144.4, 301, 112; 124/295

[56] References Cited

U.S. PATENT DOCUMENTS

| 976,883 | 11/1910 | Keagy et al. | 128/295 |
|---|---|---|---|
| 2,483,079 | 9/1949 | Williams | 128/295 |
| 3,072,125 | 1/1963 | O'Brien | 128/295 |
| 3,335,714 | 8/1967 | Giesy | 128/295 |
| 3,528,423 | 9/1970 | Lee | 128/295 |
| 3,683,914 | 8/1972 | Crowley | 128/295 |
| 3,721,243 | 3/1973 | Hesterman et al. | 128/295 |
| 3,776,235 | 12/1973 | Ratcliffe et al. | 128/295 |
| 3,804,094 | 4/1974 | Manoussos | 128/290 R |
| 3,815,581 | 6/1974 | Levin | 128/295 |
| 3,931,819 | 1/1976 | Weedle | 128/283 |

FOREIGN PATENT DOCUMENTS

| 2416036 | 4/1975 | Fed. Rep. of Germany | 128/295 |
|---|---|---|---|
| 996370 | 6/1965 | United Kingdom | 4/144.3 |

*Primary Examiner*—Robert W. Michell
*Assistant Examiner*—J. L. Krutar
*Attorney, Agent, or Firm*—Edward K. Fein; John R. Manning; Marvin F. Matthews

[57] ABSTRACT

Disclosed is a urine collection device for females comprising a collection element defining a urine collection chamber and an inlet opening into the chamber and adapted to be disposed in surrounding relation to the urethral opening of the user. A drainage conduit is connected to the collection element in communication with the chamber whereby the chamber and conduit together comprise a urine flow pathway for carrying urine generally away from the inlet. A first body of wicking material is mounted adjacent the collection element and extends at least partially into the flow pathway. The device preferably also comprises a vaginal insert element including a seal portion for preventing the entry of urine into the vagina in contact therewith.

25 Claims, 9 Drawing Figures

U.S. Patent   Jan. 27, 1981   Sheet 1 of 2   4,246,901
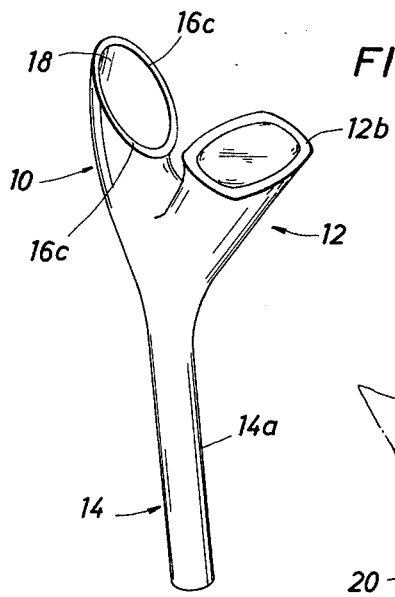
FIG. 1
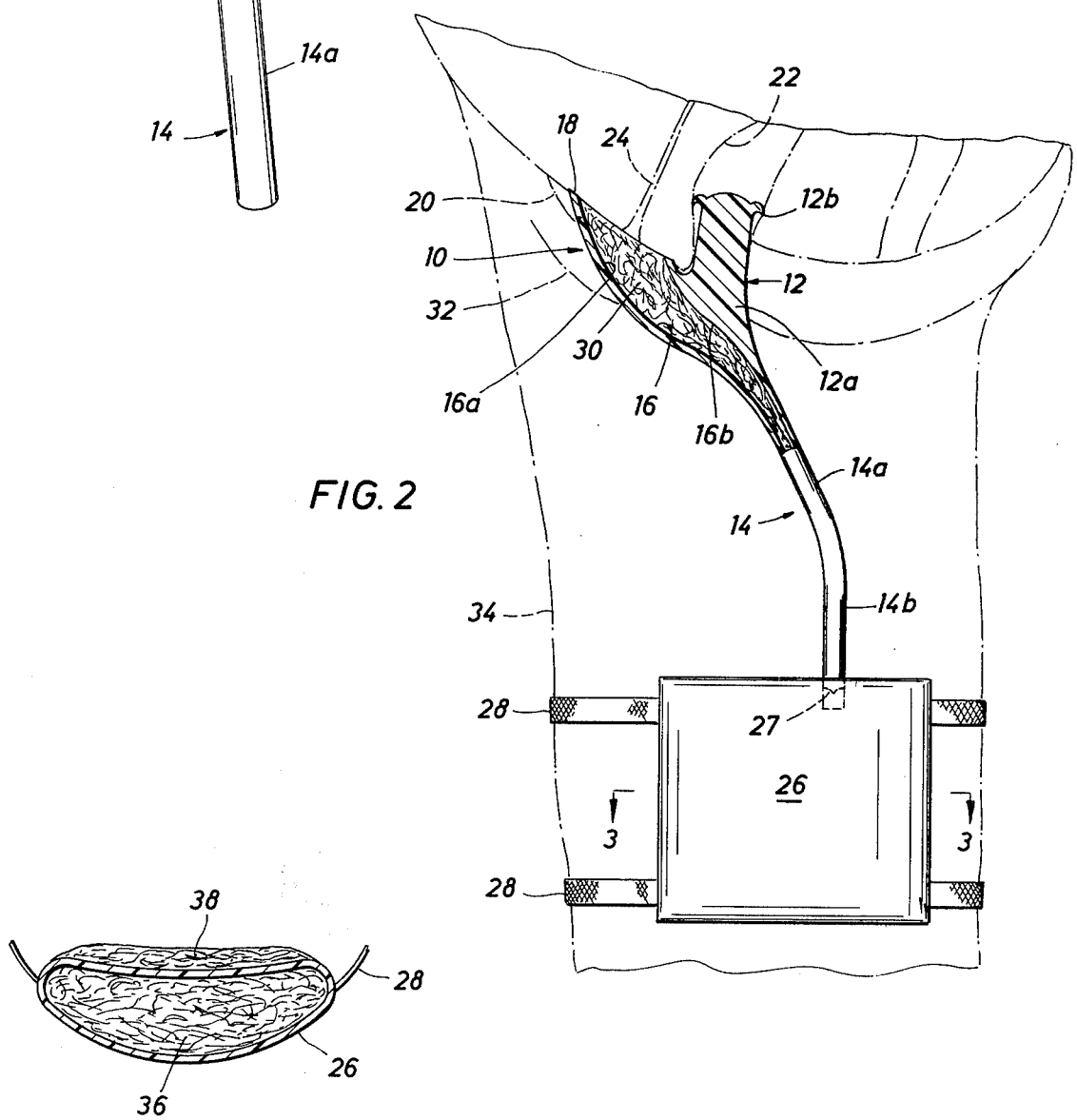
FIG. 2
FIG. 3

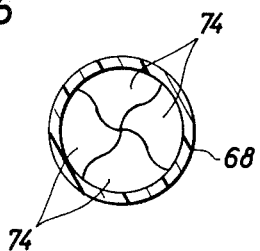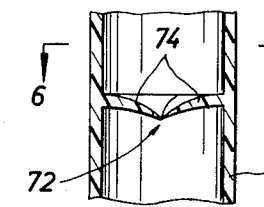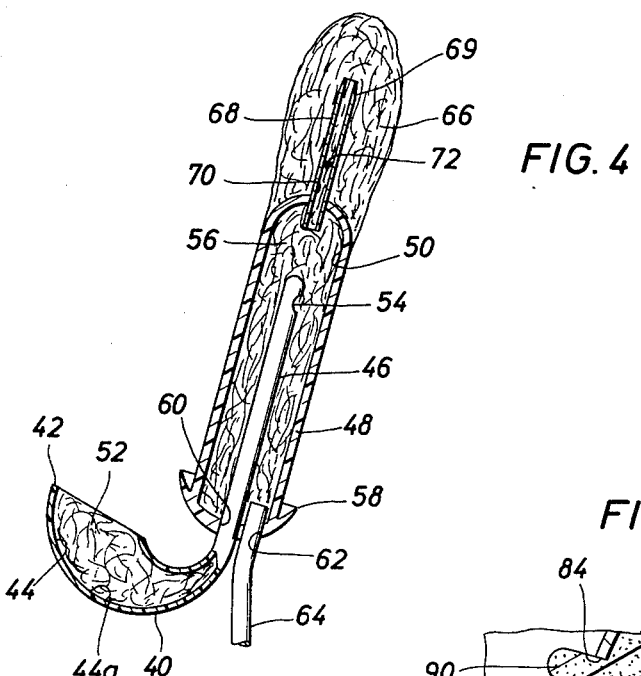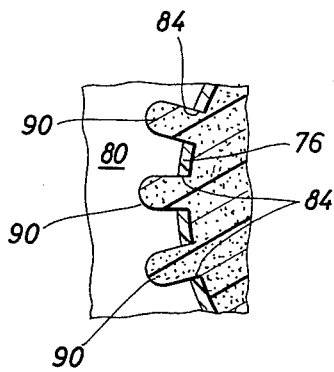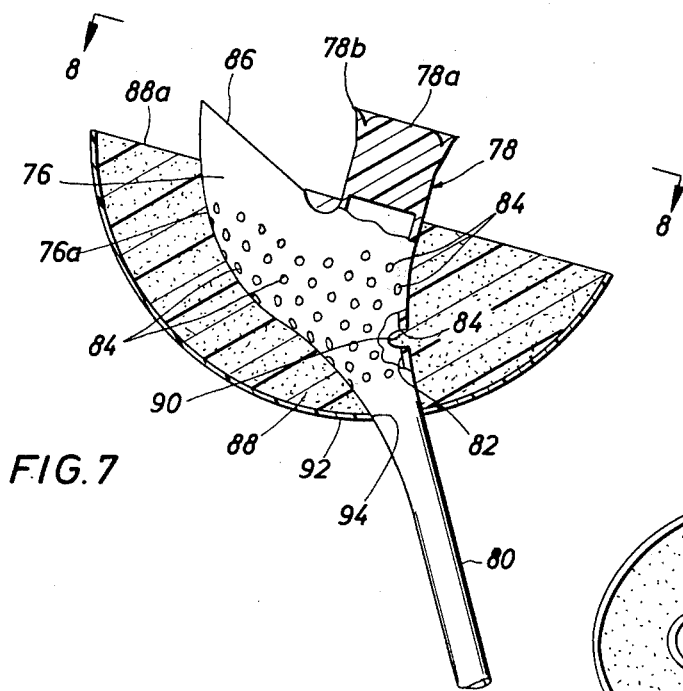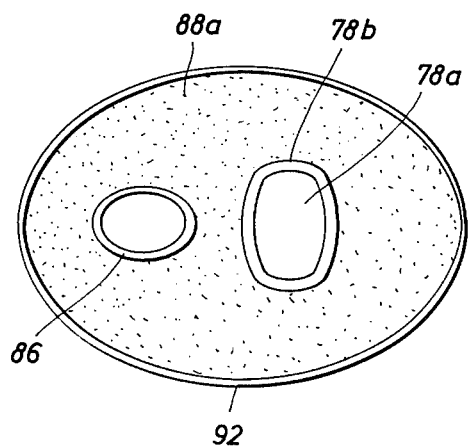

URINE COLLECTION DEVICE

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 45 U.S.C. 2457).

BACKGROUND OF THE INVENTION

1. Field of the Invention

The present invention pertains to urine collection devices for females. Such devices are needed not only by incontinent individuals but also by those who, by virtue of their particular circumstances, are precluded from using ordinary restroom facilities for extended periods of time. Examples, of the latter group are those who are incapacitated and/or bed-ridden as well as those whose occupations demand that they remain on duty and/or continuously wear special protective clothing for extended periods of time.

In providing a urine collection device for females, several particular problems must be addressed. One of these is to provide the most positive protection possible against leakage of urine from the collection system. At the same time it is necessary to limit the contact of urine with the exterior of the user's body to the greatest extent possible, both in terms of surface area of the body involved and the length of contact time. Thus it is necessary that the urine be carried away from the body quickly and completely. As corollary, it is necessary to prevent the entry of urine into the vagina in contact therewith, for the presence of urine in the vagina can lead to infection.

2. Description of the Prior Art

Known urine collection devices for females fall into several basic categories. The first of these includes absorbent garments similar to diapers and sanitary napkins. These are unacceptable for numerous reasons. They are bulky, uncomfortable and generally aesthetically offensive. The urine which is held in the garment provides an extremely effective growth medium for bacteria. They permit contact of the moist absorbent material with a large area of the body thus giving rise to irritation and even infection of the skin. They do not adequately prevent contact of urine with the vaginal opening or the interior of the vagina, particularly when used by a person reclining in a supine position, whereby even more serious infections may result from bacterial growth in the vagina. Such garments, even at their best, must be frequently changed in order to minimize the above problems, and are therefore particularly unacceptable for persons who are circumstantially prevented from attending to such matters.

A second category of urine collection devices includes cup-like receptacle members which are held in close proximity to the body to collect urine and direct it into a drain tube leading to a suitable bag or tank. A pump may or may not be provided for drawing the urine into the tank. These devices may be further subdivided into those which include a receptacle member having a rim or opening large enough to encompass virtually the entire uro-genital area. U.S. Pat. No. 3,601,125 is exemplary of this type of device. The purpose of providing the relatively wide opening is presumably to limit the leakage and discomfort which may result when an attempt is made to fit the rim against the uro-genital area. However, such devices do not accomplish these purposes since they are still susceptible to leakage problems and, furthermore, create their own brand of discomfort, particularly by interfering with the user's freedom of movement and ability to assume various postures, and by limiting her choice of clothing. Additionally, they permit urine to flow across the vaginal opening. Depending upon the position of the user, the urine may flow into the vagina and, in any event, even a single drop adhering to the vaginal opening may cause considerable bacterial growth.

A second sub-category of the receptacle type of device is exemplified by U.S. Pat. No. 3,776,235 and U.S. Pat. No. 3,683,914. In this type of device, the urine receptacle typically has a smaller rim designed to fit within the uro-genital area in much closer proximity to the urethral opening. Many such devices also include a vaginal locator for holding the device in place. While these devices may purport to seal against the entry of urine into the vagina, they are not truly effective in this respect. Meanwhile, they are even more susceptible to leakage than the larger-rimmed variety and may cause considerable discomfort due to being in contact with a more sensitive area.

Another general fault in many of the devices of both sub-categories of the receptacle-type group is that the receptacles include inner surfaces which are so configured and/or oriented in use that they aggravate the problems of urine splashing back toward the body and of turbulence in the urine.

A third general approach to the problem is catherization. This is extremely irritating and obviously unsuitable for long-term use, especially for a woman who is incontinent but otherwise healthy and active or for one whose activities are restricted due to occupation or like circumstances.

In short, the problems of such persons are both numerous and serious, and not the least of these problems are those created by the conventional urine collection apparatus itself.

SUMMARY OF THE INVENTION

The present invention provides a urine collection device including a body of wicking material disposed to absorb urine before any substantial leakage can occur and carry the urine away from contact with the user's body. In particular, the device comprises a collection element defining a urine collection chamber and an inlet into the chamber adapted to be disposed in surrounding relation to the urethal opening of the user. A drainage conduit is connected to the collection element in communication with the chamber. Thus the chamber and drainage conduit together comprise a urine flow pathway for carrying urine generally away from the inlet. The aforementioned body of wicking material is mounted adjacent the collection element and extends at least partially into the flow pathway for directing urine into and/or along the pathway.

Because of the provision of the wicking material, substantial leakage is eliminated. Accordingly, the device as a whole may be made relatively small thereby minimizing the discomfort, bulkiness, and other undesirable attributes of prior devices.

The inner walls of the collection chamber are configured to facilatate smooth flow of the urine away from the body and to avoid turbulence and splashing.

The device also preferably comprises a vaginal insert element connected to the collection element. The insert helps to properly position the device and hold it in place and also includes a seal portion for preventing entry of urine into the vagina in contact therewith.

Several different forms of the invention are provided to serve the needs of different users. For example, in one form, the body of wicking material fills the urine flow pathway and actually opposes the urethral opening in use. This form is adapted to the needs of incontinent persons in whom the volumetric flow rate is relatively small. The urine is absorbed by the wicking material virtually immediately upon its emission and carried away from contact with the user's body by the wicking material with no opportunity for substantial leakage.

If the user is so situated that the device may be changed or emptied at relatively frequent intervals, such that the device need not be adapted to hold a large quantity of urine, the vaginal insert element may be enlarged and provided with a hollow portion defining a reservoir comprising at least a portion of the drainage conduit. The reservoir prevents contact of urine with the vagina while permitting urine to be stored therein. Thus externally worn tubing, storage bags, and the like may be eliminated. The device is virtually undetectable in use and offers minimal limitations on the user's activities, choice of clothing, etc.

If the user is so situated that the device must be capable of accommodating a larger volume of fluid, the drainage conduit may extend to a storage pouch worn, for example, on the user's leg. The pouch is of an improved form which is filled with wicking material, and further provided with an exterior pad of wicking material for disposition against the user's body. The internal wicking material effects greater control of the liquid collected, while the pad provides greater comfort for the user by absorbing perspiration, etc. The pouch may also contain a bacterial static agent either in the wicking material or in another suitable medium.

For those whose volumetric flow rate of urine is greater, for example women who urinate normally but are precluded by their occupations from using ordinary facilities, placement of the wicking material within the collection chamber is undesirable since it tends to resist rapid, large volume flow. For such persons, the body of wicking material is mounted to externally surround the collection element. The body of wicking material is provided with a plurality of protuberances which extend through respective apertures in the collection chamber distal the inlet. Thus, while most of the urine will pass directly into the collection chamber through the inlet, any which leaks past the inlet will be absorbed by the wicking material and directed thereby into the collection chamber.

Accordingly, it is a principal object of the present invention to provide an improved urine collection device for females.

Another object of the invention is to provide such a device having a body of wicking material disposed adjacent the collecting element thereof.

Yet another object of the invention is to provide such a device having a collection chamber designed to minimize splashing and turbulence of urine.

A further object of the invention is to provide such a device having an improved vaginal seal.

Still another object of the invention is to provide a urine collection device having an intra-vaginal reservoir.

Yet a further object of the invention is to provide an improved urine storage pouch adapted to be worn on the user's person.

Still other objects, features, and advantages of the present invention will be made apparent by the following description of the preferred embodiments, the drawings and the claims.

BRIEF DESCRIPTION OF THE DRAWINGS

FIG. 1 is a perspective view of the interface member of a urine collection device according to a first embodiment of the invention.

FIG. 2 is a view partly in section and partly in elevation of the member of FIG. 1 incorporated into a complete collection device and in operative position on the user.

FIG. 3 is a sectional view taken on line 3—3 of FIG. 2.

FIG. 4 is a sectional view, with certain parts in elevation, of a second embodiment of the invention.

FIG. 5 is an enlarged sectional detailed view of the valve means of the embodiment of FIG. 4.

FIG. 6 is a view taken on line 6—6 of FIG. 5.

FIG. 7 is a view partly in section and partly in elevation of a third embodiment of the invention.

FIG. 8 is a plan view taken on line 8—8 of FIG. 7.

FIG. 9 is an enlarged sectional detailed view of some of the wicking protuberances and mating apertures in the embodiment of FIGS. 7 and 8.

DESCRIPTION OF THE PREFERRED EMBODIMENTS

Referring to FIGS. 1 and 2, there is shown a first embodiment of the invention. While the orientation of the device will vary in use depending on the position of the user, for convenience herein the device will be described as it would appear while in use on a person in a standing position, and terms such as "front," "rear," "upward," "downward," etc. in the specification and claims should be construed accordingly and not in a limiting sense with respect to actual positions in use. The device includes a hollow collection element 10, a vaginal insert element 12, and a drainage conduit 14. The elements 10 and 12, as well as the upper portion 14a of the conduit 14 are integrally molded into the interface member shown in FIG. 1. In use, this interface member engages the user's body, shown in phantom in FIG. 2.

The collection element 10 defines a urine collection chamber 16 having an uppermost inlet 18. Inlet 18 is preferably of oval shape, as best seen in FIG. 1, and is oriented so that the length of the oval extends generally in the ventral-dorsal direction in use. The inlet 18 is sized to fit generally between the labia minor 20 and to extend in the ventral-dorsal direction from a point slightly rearward of the clitoris to a point slightly forward of the opening to the vagina 22 in surrounding relation to the urethral opening 24. While the walls of chamber 16 and inlet 18 are shown as relatively thick for purposes of illustration, it should be understood that they would preferably be much thinner in actual practice.

Chamber 16 is generally funnel-shaped, the walls thereof being inclined generally downwardly and rearwardly from the inlet 18. As best seen in FIG. 2, these walls are more nearly upright near inlet 18 and more rearwardly inclined near the bottom of chamber 16. This configuration helps to direct the urine away from the urethral opening 24 whether the user is sitting, standing or reclining supine. The cross-sectional area of the chamber tapers down to that of the drainage conduit 14 connected thereto.

More specifically, the inner walls of chamber 16 include a forward-lower wall 16a and an upper-rear wall 16b. The uppermost and forwardmost portion of wall 16a is generally opposed to inlet 18. As shown in FIG. 2, this portion of wall 16a is downwardly and rearwardly inclined with reference to the orientation of the device when it is in place on the user, and when the user is in a standing position. It can further be seen that this same portion of wall 16a is angularly disposed with respect to the urethral opening 24, rather than being directly opposed thereto, when the device is properly positioned on the user. Such orientation of the uppermost and forwardmost portion of inner chamber wall 16a reduces the tendency of urine exiting opening 24 to splash back toward the user's body, but rather enhances a smooth downward and rearward flow of such urine while minimizing turbulence therein. Turbulence and splashing is further reduced by the fact that there are no sharp angles or the like in wall 16a. Rather, as wall 16a extends from inlet 18 to conduit portion 14a, the angles through which it passes are substantially greater than 90°. Furthermore, the wall 16a comprises smooth curved surfaces of relatively large radius providing gradial transition through such angles. Upper-rear wall 16b is similarly configured and generally tracks the configuration of wall 16a. Walls 16a and 16b are joined through smooth, relatively large radius curves by side walls 16c (see FIG. 1). Thus, the entire interior of chamber 16 is devoid of any sharp, angular configurations.

Conduit 14 has an upper portion 14a which, in the embodiment shown, is molded integrally with the collection element 10 and insert element 12 as part of the interface member. Portion 14a is angled rearwardly at about 30° with respect to vertical. This angle helps to prevent kinking of the lower portion 14b of the drainage conduit, the latter being formed of a generally more flexible material than the upper portion. The lower portion 14b of conduit 14 is removably joined and sealed to upper portion 14a in any suitable manner and extends into a urine storage pouch 26 to be described more fully below. Both portions 14a and 14b of the drainage conduit are formed of tubing having sufficient flexibility to accommodate the movements of the user but sufficient rigidity to resist collapse or kinking or so as to interfere with the flow of fluid therethrough. To this end, lower portion 14b may, as mentioned above, be made somewhat more flexible than upper portion 14a. It is further noted that the line of demarcation between the collection element 10 and upper portion 14a is somewhat arbitrary, and further that the conduit 14 could be formed in a single piece or in more than two pieces as desired. Together, chamber 16 and conduit 14 comprise a urine flow pathway from inlet 18.

A first body 30 of wicking material is removably mounted in the chamber 16 and extends therefrom into the conduit 14. The body 30 substantially fills the chamber 16 and the interior of conduit 14. By this is meant simply that the body 30 extends substantially to the limits or extremities of the chamber 16 and conduit 14 and not that it occupies all the space therein, since the porosity of the body 30 provides for receipt therein of the urine to be collected. In particular, the body 30 extends upwardly to the inlet 18 and opposes and preferably abuts the urethral opening 24. It is also noted that a "body" of wicking material, as that term is used herein, may be formed integrally or in several abutting parts.

The embodiment of FIGS. 1 and 2 is particularly suited to incontinent persons whose volumetric flow rate of urine is relatively slow. Since the body 30 abuts the urethral opening 24, each drop of urine emitted is immediately absorbed into body 30, and thus into the chamber 16. Thus the urine is prevented from clinging to the user's body and leaking rearwardly to the vaginal opening as might otherwise occur. The body 30 of wicking material will draw the urine away from the urethral opening 24 through the chamber 16 and conduit 14 to the pouch 26 regardless of the posture assumed by the user. With a large enough pouch 26 and periodic changing of the body 30, the surface of body 30 in contact with the user's body should remain relatively dry and comfortable. Furthermore, as mentioned above, the inlet 18 is relatively small whereby the portion of body 30 contacting the user's body is limited to a very small area thereof.

The insert element 12 is connected to the inclined upper-rear wall of collection element 10 at a point spaced downwardly and rearwardly from the inlet 18. The upper or free end of insert element 12 extends upwardly past inlet 18 whereby it may be inserted into the vagina 22. Element 12 includes a solid main body portion 12a and an annular resilient lip seal 12b circumscribing and extending generally radially away from the main body portion 12a adjacent the free end of the insert. In its relaxed position, shown in FIG. 1, the radially outer edge of seal 12b also extends longitudinally toward the free end of the insert. However, seal 12b is sufficiently flexible so that, as the insert element 12 is inserted into the vagina 22, the seal 12b is inverted to the position shown in FIG. 2. Thus, in use, the edge of seal 12 extends longitudinally away from the free end of the insert, i.e. outwardly toward the vaginal opening. Thus seal 12b is highly effective against the entry of any urine which should leak past inlet 18 into the vagina 22 in contact therewith. As best seen in FIG. 1, the main body portion 12a is not round in transverse configuration, but rather is laterally elongated so as to more comfortably fit the natural configuration of the vagina (compare also FIG. 7).

The insert element 12 also helps to position the interface member and retain it in place. Furthermore, the interface member is sized so that the major portion thereof, exclusive of conduit portion 14a, is disposed between the labia major 32 in use. This disposition further helps to position and retain the interface member whereby retaining straps, garments, or the like may ordinarily be eliminated. Additionally, the size and disposition of the interface member in use helps to conceal its presence thereby affording minimal limitations on the clothing and activities of the user.

The pouch 26 may be fastened about the user's leg 34 by straps 28 or secured on the person in any other suitable manner. Pouch 26 is comprised of a flexible material impervious to urine. To provide for greater control of the urine collected, and in particular to help draw the urine from the conduit 14 and prevent leaking or sloshing of urine within the pouch, the interior of the pouch is filled with a body 36 of wicking material (see FIG. 3).

An external pad 38 of wicking material is mounted on the exterior of pouch 26 on the side adapted to be disposed against the leg 34. This pad makes the pouch more comfortable and, in particular, absorbs perspiration. The pad 38 and/or the body 36 may be removable if desired. To provide for removal of body 36, the pouch 26 may include a leakproof opening of any suitable type as will be appreciated by those skilled in the art. Alternatively, the entire pouch 26, including the body 36 and pad 38, and even the conduit portion 14b, may be disposable.

The pouch 26 preferably also has a one-way check valve at its inlet, as indicated at 27 in FIG. 2. This valve is preferably of a type to be described more fully below in connection with FIGS. 5 and 6. The interior of pouch 26 preferably contains a bacterial static agent such as crystal merthiolate, copper sulfate or boric acid to limit the growth of bacteria and thereby reduce the formation of odors and other undesirable effects. The wicking material 36 within the pouch 26 may be impregnated with such bacterial static agent, or alternatively, the agent may be carried by some other suitable medium within the pouch. If desired, the wicking material within conduit 14 distal the body of the user may also be impregnated with a similar bacterial static agent.

The interface member 10, 12, 14 may be made of any suitable material which is impervious to urine and medically acceptable for close contact with the skin and mucous membranes. The material should further be sufficiently pliable to permit the user to move comfortably and to allow for flexing of the lip seal 12b. At the same time, the material must have sufficient rigidity to remain properly in place and maintain its basic configuration without collapse of the chamber 16 or conduit 14. The body 30 of wicking material may be instrumental in preventing such collapse. One example of a preferred interface material is ethyl methacrylate. This material is resistant to deterioration by or reaction with urine. Furthermore, it becomes pliable and comfortable at ordinary body temperature and pressure and actually conforms to the configuration of the user's body for optimum comfort. Another material which might be used is medical grade silicone. Conduit portion 14b may be formed, for example of surgical latex.

The wicking material used in the body 30 should also be medically acceptable. Additionally, it is highly preferable that it be a one-way wicking material arranged to draw the urine away from inlet 18, although, in some instances, a two-way wicking material may suffice. If the body is intended to be washed and re-used, various types of foams and fabrics may be used. For example, a non-reticulated, fine pore polyester urethane foam, available under the trade-name "pyrel" from Scott Foam Division of Scott Paper Co., has been found to be suitable. An example of an acceptable fabric is the type sold commercially under the trade-name "rhovil." Such materials could also be used for disposable forms of the body 30 as could less expensive materials such as cotton. It can be seen that the body 30 can be inserted or removed through the inlet 18 of the interface member. Just as the conduit 14 may be formed in several sections, the body 30 may, as mentioned above, be comprised of several pieces, preferably abutting one another.

Various types of wicking materials may also be used for the body 36 and the pad 38. The material for pad 38 should be medically acceptable for contact with the skin. A wider choice may be permitted for body 36. In any event, the choice will be influenced by whether or not the body or pad in question is to be disposable. For example, if the member is to be disposable, a relatively inexpensive material may be preferred. However, if the member is intended to be washed and re-used, a more durable foam, fabric or the like is preferred.

Referring to FIGS. 4 and 5, there is shown a second embodiment of the invention, also intended for use by incontinent persons who have a relatively small volumetric flow rate of urine. FIG. 4 shows the interface member of this embodiment. The interface member includes a collection element 40 whose inlet 42 is substantially identical to the inlet 18 of the first embodiment. Like the collection element 10, element 40 defines a urine collection chamber 44. However, while the walls of element 40 first extend downwardly and rearwardly from inlet 42, they then curve upwardly and rearwardly to meet the tubular upstream portion 46 of the drainage conduit, portion 46 being integrally molded with element 40.

FIG. 4 further shows that the inner walls of chamber 44 are defined by smooth curved surfaces of relatively large radius, as opposed to sharp and/or angular formations. It can also be seen that the inner walls include a portion 44a generally opposed to inlet 42 and angularly positioned with respect thereto. Such inner wall portion 44a is also generally downwardly and rearwardly inclined from inlet 42 in use when the user is in a standing position. As explained more fully above, such configurations and orientations tend to inhibit splashing and/or turbulence of the urine. Rather than extending downwardly to a storage pouch, conduit portion 46 extends upwardly into the vaginal insert element 48. Element 48 is much longer than the corresponding element of the embodiment of FIGS. 1–3 and is hollowed to form a urine reservoir 50 whereby urine may be stored within the vagina but without contact therewith. Thus reservoir 50 may be said to comprise a further portion of the drainage conduit.

A first body 52 of wicking material is removably mounted in and substantially fills chamber 44 and conduit portion 46. The material of body 52 is preferably a one-way wicking material arranged to draw fluid from inlet 42. Thus urine may be absorbed at inlet 42 and drawn into reservoir 50. The end of conduit portion 56 distal the collection element 40 is provided with an opening 54 through which urine may be drawn into a second body 56 of wicking material substantially filling reservoir 50. Reservoir 50 may contain a quantity of bacterial static agent in body 56 of another suitable medium.

Vaginal insert member 48 includes a main body portion, defining reservoir 50, and an annular lip seal 58 substantially identical in structure and operation to the seal 12b of the first embodiment. Member 48 is formed separately from the collection element 40 and conduit portion 46 and is provided with an opening 60 in its lower end for snugly and sealingly receiving portion 46. A second opening 62 may be provided adjacent opening 60 for similarly receiving a tube 64 leading to a pouch similar to pouch 26 of FIGS. 2 and 3. Tube 64 is preferably filled with a respective body of (preferably one-way) wicking material. By virtue of the additional storage space provided by reservoir 50, the pouch used with the embodiment of FIGS. 4 and 5 may be made smaller and less obtrusive than that of FIGS. 2 and 3. Furthermore, if the user is so situated that the device need not be capable of accommodating a large volume of urine, e.g. if she is able to change the wicking material relatively frequently, the opening 62, tube 64 and attached pouch may be eliminated altogether whereby the device is virtually undetectable in use and poses the least possible restriction of the user's choice of clothing and activities.

Member 48 may also be adapted to collect and accommodate menstrual flow by mounting a tampon-like body 66 of wicking material on its free end, as by a suitable adhesive. A tube 68 may be embedded in the body 66 and have one end extending through an opening 70 in the free end of member 48. Within tube 68 is a respective body 69 of one-way wicking material arranged to draw fluid into reservoir 50. As an additional check on reverse flow, a one-way valve 72, which permits the menstrual fluid to flow into the reservoir 50 but does not permit urine or bacterial static agent to pass out of the reservoir into the body 66, is provided in tube 68. As shown in FIGS. 5 and 6, valve 72 includes a plurality of flexible flaps 74 extending radially and longitudinally inwardly from the interior of tube 68, concave downwardly, and having their edges overlapping. Again, if the user is able to attend to the device relatively frequently, the tube 68 and its valve 72 may be omitted.

The body 66 may be removable and disposable, and the member 48 may be formed in two parts to permit removal of body 56. However, the entire insert element 48, including bodies 56 and 66 may be disposable. As in the preceding embodiment, the walls of elements 40 and 48 have been shown thicker than is actually contemplated for purposes of illustration.

Referring now to FIGS. 6-8 there is shown a third embodiment of the invention intended for use by persons who have a high volumetric urine flow rate. These may be incontinent persons who periodically emit relatively large quantities of urine or those who have no urinary problem but are precluded, as by their occupations, from using ordinary restroom facilities for long periods of time.

The embodiment of FIGS. 7-9 includes an interface member, the external configuration of which is substantially identical to that of the interface member of FIGS. 1 and 2. This member includes a collection element 76, a vaginal insert element 78, and the upper portion 80 of a drainage conduit. Internally, the interface member of FIG. 6 differs from that of FIGS. 1 and 2 in that the solid main body portion 78a of the insert element 78 extends downwardly only to about the point of juncture of the insert element 78 and collection element 76. Accordingly, the chamber 82 defined by the collection element 76 extends all the way to the rear extremity of the interface member above the conduit portion 80.

In particular, it is noted that the chamber 82 includes an inner forward-lower wall which is substantially parallel to outer wall 76a and substantially indentical in configuration to wall 16a of the embodiment of FIG. 2 including the portion thereof which is opposed to the inlet of the collection element. The tendency of such configuration to reduce splashing and turbulence of the urine becomes particularly important in the embodiment of FIGS. 7-9 since the collection chamber 82 thereof is not filled with wicking material. The walls of chamber 82 are perforated by a plurality of apertures 84 located distal the inlet 86 of the collection element 76 and, in particular, in the lower part of the chamber generally below the insert element 78.

A first body 88 of wicking material externally surrounds the collection element 76 from a point just below the inlet 86 to the lower portion of the chamber 82. Thus, body 88 surrounds the perforated portion of chamber 82. Body 88 is provided with a plurality of protuberances 90 sized and positioned to extend through respective ones of the apertures 84. Body 88 also surrounds the lower portion of insert element 78. The wicking material of the body 88 is preferably a one-way foam type which may be molded around the interface member. Body 88 may be impregnated with a bacterial static agent provided such agent is isolated from the portion of body 88 near the user's body. Body 88 may be formed in two or more separable parts for ease in assembling and disassembling the device for cleaning, replacement of the body 88, etc.

Body 88 has an upper collection surface 88a disposed to face toward, and preferably abut, the user's body in use. The remainder of body 88 is surrounded by a cup-like casing 92 formed of a material impervious to urine. The materials of both casing 92 and interface member 76, 78, 80 may be substantially similar to those of the interface members of the preceding embodiments. Body 88 and casing 92 are sized and configured so that the collection surface 88a generally opposes the entire urogenital area of the user. Conduit portion 80 extends through an opening 94 in casing 92 and thence downwardly to the lower portion of the drainage conduit (not shown) which may lead to a pouch (also not shown) similar to pouch 26 of FIGS. 1 and 3 or to any other suitable container. Insert element 78 is provided with a lip seal 78b substantially identical to seals 12b and 58 of the preceding embodiments.

In use, the major portion of any urine passed will enter the inlet 86 of the collection element and pass through chamber 82 and conduit portion 80 and ultimately into the storage pouch. A relatively large volumetric flow rate can be accommodated since the collection chamber 82 is unobstructed with wicking material which might otherwise unduly resist such high volume flow and cause leakage. However, since there is no wicking material within chamber 82, the body 88 of wicking material is provided to collection any urine which does leak past inlet 86 and direct such urine back into chamber 82 via the protuberances 90 and apertures 84. The device may be held in place on the user's body by straps secured to casing 92, by adhering the device to the under garments of the user by employing double sided adhesive tape, by a suitable garment, or in any other acceptable manner as is well known in the art.

Numerous modifications of the preferred embodiments disclosed above may be made without departing from the spirit of the invention. In particular, various features of the different embodiments may be combined, as for example by providing a device having bodies of wicking material both internal and external to the interface member.

Since optimum performance of the device is dependent on proper fitting of the interface with respect to the user's body, modifications of the configuration of the interface will be necessary to properly fit different individuals. These might involve changes in the size and shape of the inlet as well as its spacing and angular relationship to the insert element, positioning of the seal on the insert element, etc. While it is anticipated that a number of standardized configurations could be developed, one or another of which should fit most individuals, it is entirely feasible, both technically and economically, to custom make the interface member for the individual. Thus, the device could be customized for anatomically abnormal persons. For example, it could be modified for those in whom the urethral opening is located within the vagina by sizing and shaping the inlet to extend into the vagina to encompass the urethral orifice.

Still other modifications will suggest themselves to those skilled in the art. Accordingly, it is intended that the scope of the invention be limited only by the claims which follow.

What is claimed is:

1. A urine collection device for human females comprising:

a collection element defining a urine collection chamber and an inlet opening into said chamber, the portion of said collection element defining said inlet adapted to be disposed in a surrounding contacting relation to the urethral opening of the user between the labia minor and between the clitoris and the vaginal orifice, said collection element comprised of a material which is relatively rigid at at normal room temperatures, but becomes more flexible and resilient at human body temperatures such as to readily conform to the configuration of the user's anatomy when subjected to the temperature and pressure of the user's body against the material;

a drainage conduit connected to said collection element in communication with said chamber whereby said chamber and said drainage conduit together comprise a closed urine flow pathway for carrying urine generally away from said inlet;

and a first body of wicking material mounted adjacent said collection element and extending at least partially into said flow pathway.

2. The device of claim 1 wherein said chamber has an inner wall portion generally opposed to said inlet and downwardly and rearwardly inclined with reference to the orientation of said device when positioned on the user in a standing position.

3. The device of claim 2 having means engageable with the body of the user to position said inner wall portion angularly with respect to the urethral opening of the user.

4. The device of claim 3 wherein said inner wall portion extends from said inlet to said drainage conduit through angles greater than 90°.

5. The device of claim 4 wherein said inner wall portion comprises smooth curved surfaces providing gradual transitions through said angles.

6. The device of claim 1 further comprising a vaginal insert element connected to said collection element and having a free end adapted to extend into the vagina in use.

7. The device of claim 6 wherein said vaginal insert element includes a main body portion and a seal portion extending generally radially from said main body portion.

8. The device of claim 6 wherein said first body of wicking material substantially fills said chamber.

9. The device of claim 8 wherein said drainage conduit extends generally away from said vaginal insert element, and wherein said first body of wicking material extends into said drainage conduit.

10. The device of claim 8 wherein said vaginal insert element includes a hollow portion defining an enclosed reservoir therein for urine containment, said reservoir conforming to the shape of the vagina and comprising at least a portion of said drainage conduit.

11. The device of claim 10 further comprising a second body of wicking material substantially filling said reservoir.

12. The device of claim 6 wherein said first body of wicking material externally surrounds said collection element and has a collection surface disposed to face toward the user's body in use, said collection chamber having a plurality of apertures therethrough extending into said chamber and spaced from said inlet, said first body of wicking material having a plurality of protuberances extending into said chamber through respective ones of said apertures, and said device further comprising a casing element surrounding said first body of wicking material exclusive of said collection surface.

13. The device of claim 6 wherein said collection element and said vaginal insert element are integrally formed from a material which is impervious to urine and medically acceptable for intimate bodily contact.

14. The device of claim 1 wherein said wicking material is a one-way wicking material.

15. The device of claim 1 wherein said drainage conduit includes a tubular member extending away from said inlet, said device further comprising a storage pouch connected to said tubular member at an end thereof opposite said collection element and adapted to be worn on the user's person at some position distant from said collection element.

16. The device of claim 15 wherein said pouch is substantially filled with wicking material.

17. The device of claim 15 wherein said pouch has a bacterial static agent therein.

18. The device of claim 15 including an external interface pad of wicking material positioned to be disposed in between the user's body and said pouch.

19. The device of claim 1 wherein the inner walls of said chamber are configured to extend generally downwardly and rearwardly from said inlet with respect to the user's body in use.

20. The device of claim 1 wherein said first body of wicking material is removable.

21. A urine collection device for human female comprising:

a collection element defining a urine collection chamber and an inlet opening into said chamber, the portion of said collection element defining said inlet adapted to be disposed in a surrounding contacting relation to the urethral opening of the user between the labia minor and between the clitoris and the vaginal orifice;

a drainage conduit connected to said collection element in communication with said chamber whereby said chamber and said drainage conduit together comprise a closed urine flow pathway for carrying urine generally away from said inlet;

a first body of wicking material mounted adjacent said collection element and extending at least partially into said flow pathway;

a vaginal insert element connected to said collection element and having a free end adapted to extend into the vagina in use, said vaginal insert element including a main body portion and a seal portion extending generally radially from said main body portion; and wherein said seal portion comprises a continuous resilient lip circumscribing said main body portion and having a radially outer edge, said lip having an operative position in which said outer edge is directed longitudinally away from said free end of said vaginal insert element.

22. The device of claim 8 wherein said lip has a relaxed position in which said outer edge is directed longitudinally toward said free end of said vaginal insert element, said lip being characterized by sufficient resiliency to permit inversion to said operative position upon insertion into the vaginal opening for use.

23. A urine collection device for human females comprising:
   a collection element defining a urine collection chamber and an inlet opening into said chamber, the portion of said collection element defining said inlet adapted to be disposed in a surrounding contacting relation to the urethral opening of the user between the labia minor and between the clitoris and the vaginal orifice;
   a drainage conduit connected to said collection element in communication with said chamber whereby said chamber and said drainage conduit together comprise a closed urine flow pathway for carrying urine generally away from said inlet;
   a first body of wicking material mounted adjacent said collection element, substantially filling said chamber, and extending at least partially into said flow pathway,
   a vaginal insert element connected to said collection element and having a freeend adapted to extend into the vagina in use, said vaginal insert element including a hollow portion defining an enclosed reservoir therein for urine containment, said reservoir conforming to the shape of the human female vagina and comprising at least a portion of said drainage conduit; and wherein said drainage conduit further comprises a tubular member extending from said chamber into said reservoir, said first body of wicking material substantially filling said tubular member.

24. A urine collection device for human females comprising:
   a collection element defining a urine collection chamber and an inlet opening into said chamber, the portion of said collection element defining said inlet adapted to be disposed in a surrounding contacting relation to the urethral opening of the user between the labia minor and between the clitoris and the vaginal orifice;
   a drainage conduit connected to said collection element in communication with said chamber whereby said chamber and said drainage conduit together comprise a closed urine flow pathway for carrying urine generally away from said inlet;
   a first body of wicking material mounted adjacent said collection element, substantially filling said chamber, and extending at least partially into said flow pathway,
   a vaginal insert element connected to said collection element and having a free end adapted to extend into the vagina in use, said vaginal insert element including a hollow portion defining an enclosed reservoir therein for urine containment, said reservoir conforming to the shape of the human female vagina and comprising at least a portion of said drainage conduit; and a third body of wicking material mounted on the exterior of said vaginal insert element adjacent the free end thereof.

25. The device of claim 24 further comprising valve means operative to permit fluid flow from said third body of wicking material to said second body of wicking material but prevent fluid flow from said second body of wicking material to said third body of wicking material.

* * * * *